United States Patent [19]

Laffan et al.

[11] Patent Number: 5,276,164
[45] Date of Patent: Jan. 4, 1994

[54] PROCESS FOR THE PRODUCTION OF 4-HYDROXY-2-OXOPYRROLIDIN-1-YL-ACETAMIDE

[75] Inventors: David Laffan, Visp; Markus Banziger, Brig; John McGarrity, Visp, all of Switzerland

[73] Assignee: Lonza Ltd., Gampel/Valais, Switzerland

[21] Appl. No.: 791,196

[22] Filed: Nov. 13, 1991

[51] Int. Cl.$^5$ .................. C07D 207/38; C07D 207/273
[52] U.S. Cl. ........................................ 548/544; 548/543
[58] Field of Search ................................ 548/544, 543

[56] References Cited

U.S. PATENT DOCUMENTS

| | | | |
|---|---|---|---|
| 4,118,396 | 10/1978 | Pifferi et al. | 260/326.43 |
| 4,124,594 | 11/1978 | Monguzzi et al. | 260/326.43 |
| 4,173,569 | 11/1979 | Banfi et al. | 260/326.43 |
| 4,629,797 | 12/1986 | Pinza et al. | 548/544 |
| 4,686,296 | 8/1987 | Iriuchijima et al. | 548/544 |
| 4,780,545 | 10/1988 | Meul et al. | 548/544 |
| 4,788,294 | 11/1988 | Duc et al. | 548/544 |
| 4,788,300 | 11/1988 | Pinza et al. | 549/419 |
| 4,797,496 | 1/1989 | Pinza et al. | 548/544 |
| 4,824,861 | 4/1989 | Pinza et al. | 548/544 |
| 4,824,966 | 4/1989 | Meul et al. | 548/544 |
| 4,843,166 | 6/1989 | Meul | 548/544 |
| 4,849,528 | 7/1989 | Meul | 548/544 |
| 4,868,314 | 9/1989 | Meul | 548/547 |
| 4,877,884 | 10/1989 | Meul | 548/544 |
| 4,879,393 | 11/1989 | Meul | 548/544 |
| 4,880,940 | 11/1989 | Meul et al. | 548/544 |

FOREIGN PATENT DOCUMENTS

| | | |
|---|---|---|
| 0154490 | 9/1985 | European Pat. Off. |
| 0156655 | 10/1985 | European Pat. Off. |
| 0216324 | 4/1987 | European Pat. Off. |
| 0223328 | 5/1987 | European Pat. Off. |
| 0224256 | 6/1987 | European Pat. Off. |
| 0249018 | 12/1987 | European Pat. Off. |
| 0252353 | 1/1988 | European Pat. Off. |
| 0301398 | 2/1989 | European Pat. Off. |
| 599151 | 5/1978 | Switzerland |
| 668066 | 11/1988 | Switzerland |

OTHER PUBLICATIONS

Pifferi et al., Il Farmaco, Ed., Sc., (1977), 32, pp. 602–613.

*Primary Examiner*—David B. Springer
*Attorney, Agent, or Firm*—Fisher, Christen & Sabol

[57] ABSTRACT

Process for the production of 4-hydroxy-2-oxoyrrolidin-1-yl-acetamide, a cerebrally active pharmaceutical agent. A 4-halo-3-alkoxy-butenoic acid ester is reacted with glycine to new intermediate products of the formula:

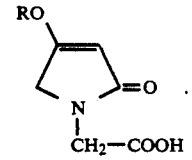

There is further by acid hydrolysis of the alkoxy group, subsequent hydrogenation, esterification of the carboxyl function and finally conversion to the end product by reaction with ammonia.

12 Claims, No Drawings

PROCESS FOR THE PRODUCTION OF 4-HYDROXY-2-OXOPYRROLIDIN-1-YL-ACETAMIDE

BACKGROUND OF THE INVENTION

1. Field Of The Invention

The invention relates to new processes for the production of 4-hydroxy-2-oxopyrrolidin-1-yl-acetamide of formula:

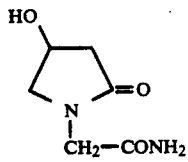

as well as to 4-($C_1$–$C_4$)-alkoxy-3-pyrrolin-2-on-1-yl-acetic acids as new intermediate products.

2. Background Art

-Hydroxy-2-oxopyrrolidin-1-yl-acetamide is a cerebrally active pharmaceutical agent, which is known under the name oxiracetam [Pifferi et al., Il Farmaco, Ed. Sc., (1977), 32, page 602]. Numerous syntheses are known for producing such active ingredient.

Thus, from European Published Patent Application No. 224256, it is known to react a 4-halo-3-($C_1$–$C_2$)-alkoxy-2E-butenoic acid-$C_1$–$C_4$ alkyl ester with a glycin ester to the corresponding 4-($C_1$–$C_2$)-alkoxy-3-pyrrolin-2-on-1yl-acetic acid alkyl ester. From Swiss Patent No. 668066, it is known to hydrogenate this ester with the help of a palladium catalyst with hydrogen, then to remove the alkoxy groups with trichloromethylsilane and sodium iodide and to react the resultant 4-hydroxy-2-oxopyrrolidine acetate with ammonia to provide the end product. From European Patent Appln. No. 216325, it is further known to hydrolyze the alkoxy group in a 4-($C_1$–$C_2$)-alkoxy-3-pyrrolin-2-on-1-yl-acetic acid alkyl ester, to hydrogenate the resultant 2,4-dioxopyrrolidin-1-yl-acetic acid alkyl ester with sodium borohydride and to react the formed 4-hydroxy-2-oxopyrrolidin-1-yl acetate finally with ammonia to provide the end product. The known syntheses have the drawback that undesirable 2-oxopyrrolidin-1-yl-acetic acid derivatives occur, particularly in the hydrogenation step, inconsiderable amounts, which can be separated from the respective reaction mixture only with much difficulty and at great expense.

From an ecological viewpoint, the reaction with glycine ester, known according to European Patent Appln. No. 224256, has additionally the drawback that the reaction necessarily has to be performed in organic solvents to achieve a satisfactory result.

BROAD DESCRIPTION OF THE INVENTION

The main object of the invention therefore was to develop a synthesis for 4-hydroxy-2-oxopyrrolidin-1-yl-acetamide, which does not exhibit the prior art drawbacks noted above and is suitable to be reacted on an industrial scale. Other objects and advantages of the invention are set out herein or are obvious herefrom to one skilled in the art.

The objects and advantages of the invention are achieved by the processes and compounds of the invention.

The invention involves a process for the production of 4-hydroxy-2-oxopyrrolidin-1-yl-acetamide of the formula:

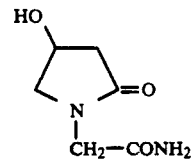

4-Halo-3-($C_1$–$C_2$)-alkoxy-2E-butenoic acid-$C_1$–$C_4$ alkyl ester is reacted with glycine into a 4-($C_1$–$C_4$)-alkoxy-3-pyrrolin-2-on-1-yl-acetic acid of the formula:

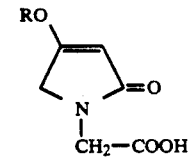

wherein R is a ($C_1$–$C_4$)-lower alkyl. The alkoxy groups are acid-hydrolyzed. The resultant 2,4-dioxopyrrolidin-1-yl-acetic acid is hydrogenated with hydrogen in the presence of a hydrogenating catalyst. The formed 4-hydroxy-2-oxopyrrolidin-1-yl-acetic acid is esterified. Alternatively, 2,4-dioxopyrrolidin-1-yl-acetic acid-($C_1$–$C_4$)-alkyl ester is hydrogenated with hydrogen in the presence of a hydrogenating catalyst. The 4-hydroxy-2-oxopyrrolidin-1-yl acetate resultant from either reaction scheme is reacted with ammonia in a known way to the end product.

In the first alternative, preferably the reaction is performed with glycine in water and in the presence of a base at a pH between 7 and 13. In the first alternative, preferably, the reaction is performed with glycine at temperatures between 50° and 100° C. In the first alternative, preferably, the acid hydrolysis in aqueous mineral acid is performed at temperatures between 0° and 100° C. In the first alternative, preferably, the 2,4-dioxopyrrolidin-1-yl-acetic acid is not isolated from the reaction mixture. Preferably, the hydrogenation is performed in acid, aqueous medium in both alternatives or variants with a ruthenium catalyst, applied on an inert support. Preferably, the hydrogenation is performed at a pressure between 5 and 50 bars and at a temperature between 0° and 70° C. In the first alternative, preferably, the esterification takes place with an aliphatic alcohol having up to 4 C atoms, either in the presence of a mineral acid or with thionyl chloride, at a temperature between 20° C. and the reflux temperature of the respective alcohol.

The invention also includes 4-($C_1$–$C_4$)-alkoxy-3-pyrrolin-2-on-1-yl-acetic acids of the formula:

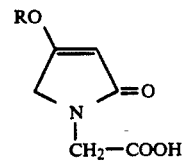

wherein R is a ($C_1$–$C_4$)-lower alkyl. R is preferably methyl or ethyl. The compounds are intermediate products in the invention process.

DETAILED DESCRIPTION OF THE INVENTION

According to the first alternative of the invention process, a 4-halo-3-($C_1$–$C_4$)-alkoxy-2E-butenoic acid-$C_1$–$C_4$ alkyl ester, preferably 4-chloro-3-methoxy-2E-butenoic acid methyl ester, is reacted with glycine into the corresponding 4-($C_1$–$C_4$)-alkoxy-3-pyrrolin-2-on-1-yl-acetic acid of formula:

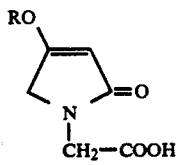

II wherein R is a ($C_1$–$C_4$)-lower alkyl, preferably methyl or ethyl. These intermediate products are new and a component of the invention.

The reaction with glycine is suitably performed in water as the solvent in the presence of a base so that the pH of the reaction mixture moves (range) between 7 and 13 during the reaction. Suitable bases are alkali or alkaline earth hydroxides, carbonates or bicarbonates. Preferably, sodium hydroxide is used as the base. The reaction temperature suitably ranges between 50° and 100° C. The 4-($C_1$–$C_4$)-alkoxy-3-pyrrolin-2-on-1-yl-acetic acids can be isolated from the reaction mixture in the usual way, but optionally can also directly be used for the next step without isolation.

In the next step, the alkoxy group is acid-hydrolyzed. Suitably, this hydrolysis is performed in aqueous mineral acids, such as, aqueous hydrochloric acid, hydrobromic acid, sulfuric acid, nitric acid or phosphoric acid, preferably in aqueous hydrochloric acid, at a temperature between 0° and 100° C. The resultant 2,4-dioxopyrrolidin-1-yl-acetic acid usually is not isolated, but fed directly to the hydrogenation. The hydrogenation takes place with hydrogen in the presence of a hydrogenating catalyst. As the hydrogenating catalyst, the usual catalyst systems, such as, platinum, ruthenium or rhodium, can be used on suitable, inert supports, such as, carbon, aluminum oxide or silica gel. Especially advantageous results were achieved with a ruthenium catalyst, applied in an amount of 1 to 10 percent of the carbon as a support. Suitably, the reaction is performed in an aqueous acid medium, preferably in the medium used in the preceding hydrolysis, in a PH range between 0 and 2, at a temperature between 0° and 70° C. and at a hydrogen pressure between 5 and 50 bars. The formed 4-hydroxy-2-oxopyrrolidin-1-yl-acetic acid can be isolated in the usual way. But preferably, it is fed directly to the esterification step.

The esterification takes place suitably with lower aliphatic alcohols having up to 4 C atoms, such as methanol, ethanol, propanol and its isomers or butanol and its isomers. Preferably, ethanol is used. The esterification can be performed either in the presence of a mineral acid, such as, sulfuric acid, or in the presence of thionyl chloride. If esterification is performed in the presence of a mineral acid, in addition, a suitable solvent, such as, cyclohexane, toluene, benzene or hexane, is advantageously added to remove the reaction water azeotropically from the reaction mixture. The esterification is suitably performed at a temperature between 20° C. and the reflux temperature of the respective alcohol, preferably at the reflux temperature of the alcohol. Preferably, the esterification is performed in the presence of thionyl chloride.

The resultant 4-hydroxy-2-oxopyrrolidin-1-yl-acetic acid-($C_1$–$C_4$)-alkyl ester by the usual working up of such ester with ammonia is converted to the end product.

As the second alternative of the invention process, the 4-hydroxy-2-oxopyrrolidin-1-yl-acetic acid-($C_1$–$C_4$)-alkyl ester is produced by hydrogenation of a 2,4-dioxopyrrolidin-1-yl-acetic acid-($C_1$–$C_4$)-alkyl ester. The 2,4-dioxopyrrolidin-1-yl-acetic acid-($C_1$–$C_4$)-alkyl ester can be synthesized in the known way according to European Published Patent Application No. 216325. In this case, the hydrogenation is suitably performed corresponding to the first alternative or variant of the invention process, as described above. The resultant 4-hydroxy-2-oxopyrrolidin-1-yl-acetic acid-($C_1$–$C_4$)-alkyl ester by the usual working up of such ester with ammonia is converted to the end product.

It has been shown that in the hydrogenation of 2,4-dioxopyrrolidin-1-yl-acetic acid alkyl ester according to the second alternative, a mixture of such ester with 4-hydroxy-2-oxopyrrolidin-1-yl-acetic acid can accumulate. Then, the resultant reaction mixture is suitably subjected to an additional esterification step corresponding to the first alternative or variant of the invention process, as described above.

The final step (of both alternatives of the invention process), that is, the reaction with ammonia, takes place in a known way, e.g., according to European Published Patent Application No. 224256.

According to the process of the invention, 4-hydroxy-2-oxopyrrolidin-1-yl-acetamide can be obtained in good overall yields and in very high purity.

EXAMPLE 1

Production of 4-methoxy-3-pyrrolin-2-on-1-yl-acetic acid 30 g (400 mmol) of glycine was suspended in 60 ml of $H_2O$ and heated to 70° C. 10M of NAOH was added with an autotitrator up to pH 8.5. Then, 22.4 g (136 mmol) of 4-chloro-3-methoxy-but-2E-enoic acid methyl ester was added at 70° to 75° C. The pH was kept constant at 8.5 by adding 10M of NAOH. After 1 hour, another 22.4 g (136 mmol) of 4-chloro-3-methoxy-but-2E-enoic acid methyl ester was added, and, after another hour, 22.4 g (136 mmol) of 4-chloromethoxy-but-3E-enoic acid methyl ester again was added. After the final addition, the reaction mixture was stirred for another 3.5 hours at 70° to 75° C. The consumption of 10M of NAOH was then 80.3 ml, which corresponded to 2 equivalents relative to the glycine used. The reaction mixture was cooled to room temperature and diluted with 40 ml of $H_2O$. Then, the reaction mixture was adjusted to pH 1 with concentrated HCl. The product precipitated after a short time, was filtered off and washed with saturated NaCl solution. After drying, 70.9 g of product was obtained. 3.41 g of product was obtained from the mother liquor. The total yield was 84 percent. The crude product was recrystallized from isopropanol: 68 g was recrystallized from 450 ml of isopropanol. 47 g of product, which corresponded to an 87 percent yield, was obtained. The product contained less than 0.01 percent of Cl. Other data for the product was:

Melting point: 164.0° to 164.5° C.

$^1$H-NMR: (D$^6$-DMSO) 3.78 (s, 3H); 3.98 (s, 2H), 4.02 (s, 2H); 12.75 (br.s, 1H)

EXAMPLE 2

Production of 4-hydroxy-pyrrolidin-2-on-1-yl-acetic acid 2.0 g (11.7 mmol) of 4-methoxy-3-pyrrolin-2-on-1-yl-acetic acid was dissolved in 15 ml of HCl (1N) at room temperature and heated to 70° C. with stirring. After 1 hour, 2.04 g of sodium acetate was added to adjust the PH to 2.0. 100 mg of Ru/C was added to the reaction mixture. The reaction mixture was transferred to an autoclave and hydrogenated at 10 bars of H$_2$ pressure with stirring. After 18 hours, the catalyst was filtered off by suction and the filtrate was concentrated by evaporation in a vacuum. The latter yielded 2.9 g of a crude mixture of NaCl and 4-hydroxy-pyrrolidin-2-on-1-yl-acetic acid (42 percent content, 60 percent yield).

EXAMPLE 3

Production of 2,4-dioxopyrrolidin-1-yl-acetic acid ethyl ester 50.0 g (250 mmol) of 4-methoxy-3-pyrrolin-2-on-1-yl ethyl acetate was dissolved in 240 ml of acetic acid at room temperature. HCl gas was introduced into the reaction mixture until saturation. The autoclave was closed and heated to 40° C. After 16 hours, the reaction mixture was cooled to room temperature and concentrated by evaporation in a vacuum so that a solution of 2,4-dioxopyrrolidin-1-yl ethyl acetate in acetic acid (50.7 g, 100 percent according to NMR) was obtained.

EXAMPLE 4

Production of 2,4-dioxopyrrolidin-1-yl-acetic acid 25 g (125 mmol) of 4-methoxy-pyrrolidin-2-on-1-yl ethyl acetate was dissolved in 120 ml of acetic acid and 2.25 ml of water (125 mmol) at room temperature in an autoclave. HCl gas was introduced into the reaction mixture until saturation. The autoclave was closed and heated to 40° C. After 20 hours, the reaction mixture was cooled to room temperature and concentrated by evaporation in a vacuum, so that a solution of 2,4-dioxopyrrolidin-1-yl-acetic acid in acetic acid (30.2 g, 100 percent according to NMR) also was obtained.

EXAMPLE 5

Production of 4-hydroxy-pyrrolidin-2-on-1-yl ethyl acetate 10.0 g (49.3 mmol) of the solution obtained according to Example 3, containing (49.3 mmol) of 2,4-dioxopyrrolidin-1-yl ethyl acetate in acetic acid, was dissolved in 100 ml of a 9:1 H$_2$O/acetic acid solution. To the reaction mixture, 500 mg of 5 percent Ru/C catalyst was added. The reaction mixture was hydrogenated at 25 bars of H$_2$ pressure with stirring. After 8 hours, the mixture was filtered and concentrated by evaporation in a vacuum. The latter yielded a mixture of 4-hydroxy-pyrrolidin-2-on-1-yl acetate and 4-hydroxy-pyrrolidin-2-on-1-yl-acetic acid. The crude mixture, in 40 ml of ethanol, was added to a solution of 10.7 (9 mmol) of thionyl chloride in 50 ml of ethanol at 0° C. The reaction mixture was refluxed and boiled for 1 hour at reflux. Then, the ethanol was distilled off. The residue was dissolved in 20 ml of water and adjusted to pH 7 with NAOH (2N). The aqueous phase was extracted for 8 hours with toluene and then for 4 hours with methylene chloride. The methylene chloride phase was concentrated by evaporation in a vacuum. After an activated carbon treatment, the latter yielded 5.6 g of 4-hydroxy-pyrrolidin-2-on-1-yl acetate (92.8 percent content, 56 percent yield).

EXAMPLE 6

Production of 4-hydroxy-pyrrolidin-2-on-1-yl ethyl acetate

A reaction mixture, consisting of 3.05 g (19.3 mmol) of 4-hydroxy-pyrrolidin-2-on-1-yl-acetic acid, 20 ml of ethanol, 0.5 ml of H$_2$SO$_4$ and 100 ml of cyclohexane, was refluxed for 4 hours. The reaction water was separated out in a water separator. The reaction mixture was completely concentrated by evaporation. Then, the residue was dissolved in 35 ml of 10 percent NaCl in H$_2$O, neutralized with NAOH and extracted continuously with tetrahydrofuran for 18 hours. The organic phase was dried on MgSO$_4$ and concentrated by evaporation on a rotary evaporator. After drying in a high vacuum, 2.83 g of product was obtained.

EXAMPLE 7

Production of 4-hydroxy-pyrrolidin-2-on-1-yl-acetamide (Oxiracetam)

3.5 g (18.8 mmol) of 4-hydroxy-pyrrolidin-2-on-1-yl ethyl acetate was dissolved in 35 ml of ethanol and mixed with 14 g of liquid ammonia. The mixture was stirred (pressure 6 bars) in an autoclave at 50° C. for 16 hours. The reaction mixture was cooled to room temperature and the excess ammonia was removed. The obtained suspension was concentrated by evaporation on a rotary evaporator and dried in a high vacuum. 2.95 g of Oxiracetam (99 percent) was obtained. Other data on the product was:

HPLC content: 97.1 percent
Melting point: 165° to 167° C.

What is claimed is;

1. A process for the production of 4-hydroxy-2-oxopyrrolidin-1-yl-acetamide of the formula:

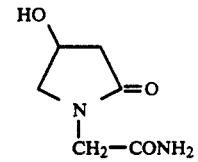

consisting essentially of:
(I) (a) reacting 4-halo-3(C$_1$–C$_2$)-alkoxy-2E-butenoic acid-C$_1$–C$_4$ alkyl ester with glycine into a 4-(C$_1$–C$_4$)-alkoxy-3-pyrrolin-2-on-1-yl-acetic acid of the formula:

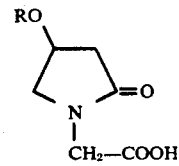

wherein R is a (C$_1$–C$_4$)-lower alkyl in water, in the presence of an alkali or alkaline earth base at a pH between 7 and 13 and at a temperature between about 50° C. and 100° C., (b) acid-hydrolyzing the alkoxy groups in the 4-(C$_1$-C$_4$)-alkoxy-3-pyrrolin-2-on-1-yl acetic acid of formula I at a temperature between 0° and 100° C. to provide 2,4-dioxopyrrolidin-1-yl-acetic acid, (c) hydrogenating the 2,4-dioxopyrrolidin-1-yl-acetic acid with hydrogen in the presence of a noble metal hydrogenating catalyst at a pressure between 5 and 50 bars and at a temperature between about 0° and 70° C. to provide 4-hydroxy-2-oxopyrrolidin-1-yl-acetate, and (d) esterifying the 4-hydroxy-2-oxopyrrolidin-1-yl-acetic acid with an lower alkanol having up to 4 C atoms at a temperature between 20° C. and the reflux temperature of the lower alkanol in the presence of an aqueous mineral acid or aqueous thionyl chloride to provide 4-hydroxy-2-oxopyrrolidin-1-yl-acetate; and (II) reacting the 4-hydroxy-2-oxopyrrolidin-1-yl-acetic with ammonia to provide the 4-hydroxy-2-oxopyrrolidin-1-yl-acetamide.

2. The process according to claim 1 wherein the base in step (a) is an alkali hydroxide, an alkali carbonate, an alkali bicarbonate, an alkaline earth hydroxide, and alkaline earth carbonate or an alkaline earth bicarbonate.

3. The process according to claim 1 wherein the acid hydrolysis in step (b) is done in aqueous mineral acid.

4. The process according to claim 3 wherein the sequence mineral acid is aqueous hydrochloric acid, aqueous hydrobromic acid, aqueous sulfuric acid, aqueous nitric acid or aqueous phosphoric acid.

5. The process according to claim 1 wherein the 2,4-dioxopyrrolidin-1-yl-acetic acid is not isolated from the reaction mixture.

6. The process according to claim 1 wherein, in step (c), the hydrogen catalyst is platinum on an inert support, ruthenium on an inert support or rhodium on an inert support.

7. The process according to claim 1 wherein the inert support is carbon, aluminum oxide or silica gel.

8. The process according to claim 6 wherein the hydrogenation is performed in an acid aqueous medium with a ruthenium catalyst, applied on an inert support.

9. The process according to claim 1 wherein, in step (c), the hydrogenation is performed in an acid aqueous medium in a pH range between 0 and 2.

10. The process according to claim 1 wherein, in step (d), the lower aliphatic alcohol which is selected from the group consisting of methanol, ethanol, propanol, an isomer of propanol, butanol and an isomer butanol.

11. The process according to claim 1 wherein, in step (d), the esterification is performed in the presence of thionyl chloride or a mineral acid.

12. The process according to claim 11 wherein the mineral acid is used in the presence of cyclohexane, toluene, benzene or hexane as a solvent.

* * * * *